United States Patent [19]

Mörsdorf et al.

[11] Patent Number: 5,039,675
[45] Date of Patent: Aug. 13, 1991

[54] BENZIMIDAZOLES AND PHARMACEUTICAL PREPARATIONS CONTAINING THESE COMPOUNDS

[75] Inventors: Peter Mörsdorf, Langenzenn; Helmut Schickaneder, Eckental; Rolf Herter, Schwabach; Volker Pfanhlert, Nuremberg; Geidrun Engler, Cadolzburg; Kurt H. Ahrens, Nuremberg, all of Fed. Rep. of Germany

[73] Assignee: Heumann Pharma GmbH & co., Nuremberg, Fed. Rep. of Germany

[21] Appl. No.: 497,223

[22] Filed: Mar. 22, 1990

Related U.S. Application Data

[62] Division of Ser. No. 168,273, Mar. 15, 1988, Pat. No. 4,957,920.

[30] Foreign Application Priority Data

Oct. 8, 1987 [DE] Fed. Rep. of Germany ....... 3734083

[51] Int. Cl.$^5$ .................... C07D 401/14; A61K 31/50
[52] U.S. Cl. .................................. 514/252; 544/238; 544/239
[58] Field of Search ................ 544/238, 239; 514/252, 514/247

[56] References Cited

U.S. PATENT DOCUMENTS 4,923,869 5/1990 Poücher et al. .................... 544/238

Primary Examiner—Nicholas S. Rizzo
Attorney, Agent, or Firm—Burns, Doane, Swecker & Mathis

[57] ABSTRACT

New benzimidazoles correponding to the general formula I

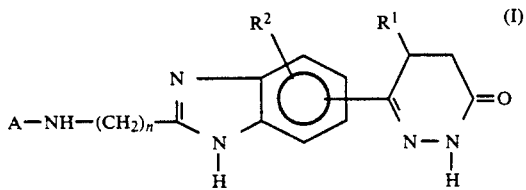

are described, in which the pyridazinone ring is attached in the 5- or 6- position of the benzimidazole ring and $R^1$ denotes a hydrogen atom or a straight chained or branched $C_1$ to $C_4$ alkyl group, $R^2$ denotes a hydrogen atom, a straight chained or branched $C_1$ to $C_4$ alkyl group, a $C_1$ to $C_4$ alkoxy group, a hydroxy group, a halogen atom, an amino group or a nitro group, A denotes a hydrogen atom, a group of the formula

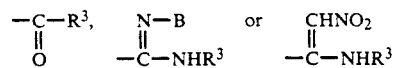

wherein $R^3$ denotes a hydrogen atom, an optionally substituted $C_1$ to $C_4$ alkyl group or a $C_1$ to $C_4$ alkoxy group and B denotes a cyano group, a benzoyl group or a phenylsulphonyl group, or A denotes a group of the formula

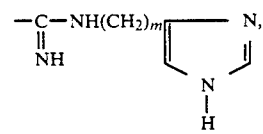

in which m has the value 2 or 3 and n represents an integer from 1 to 6, and the physiologically acceptable salts thereof as well as processes for their preparation and pharmaceutical preparations. containing these compounds These compounds are new, effective, positive inotropic substances which do not act by the mechanism of phosphodiesterase inhibition.

6 Claims, No Drawings

BENZIMIDAZOLES AND PHARMACEUTICAL PREPARATIONS CONTAINING THESE COMPOUNDS

This is a division of application Ser. No. 168,273, filed Mar. 15, 1988, now U.S. Pat. No. 4,957,920.

DESCRIPTION

The treatment of cardiac insufficiency by means of medicaments has for almost 200 years been based on the use of digitalis glycosides such as digoxin and digitoxin because these were the only substances available which had an inotropic increasing action and therefore provided the only possibility of treating the cause of cardiac failure, namely the insufficient contractibility of the heart.

The quest for digitalis substitutes initially led to the sympathomimetic drugs, but these have numerous serious disadvantages, such as undesirable chronotropic and arrhythmogenic side effects and lack of availability in a suitable form for oral administration. In the last ten years, numerous substances have been found in rapid succession which produce a positive inotropic effect, i.e. a contractibility enhancing effect by inhibiting the phosphodiesterases of the heart muscle cells, in particular phosphodiesterase type III (PDE III). Examples of these PDE inhibitors are amrinone (J. R. Benotti et al, N. Engl. J. Med. 299, 1373 (1978)), milrinone (A. A. Alousi et al, J. Cardiovasc. Pharmacol 5, 792 (1983)) and the benzimidazole derivative pimobendane (J. C. A. von Meel, Arzneim-Forsch. 35, 284 (1985)). These substances, however, also have undesirable side effects due to the mechanisms of their action, such as thrombocytopaenia or gastrointestinal disturbances.

It is therefore an object of the present invention to find new, effective, positive inotropic substances which do not act by the mechanism of phosphodiesterase inhibition.

The present invention solves this problem.

This invention relates to benzimidazoles corresponding to the general formula I

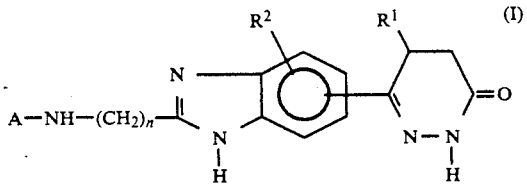

in which the pyridazinone ring is attached in the 5- or 6-position of the benzimidazole ring and $R^1$ denotes a hydrogen atom or a straight chained or branched $C_1$ to $C_4$ alkyl group; $R^2$ denotes a hydrogen atom, a straight chained or branched $C_1$ to $C_4$ alkyl group, a $C_1$ to $C_4$ alkoxy group, a hydroxy group, a halogen atom, an amino group or a nitro group: A stands for a hydrogen atom or a group of the formula

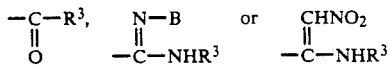

wherein $R^3$ denotes a hydrogen atom or an optionally substituted $C_1$ to $C_4$ alkyl group or a $C_1$ to $C_4$ alkoxy group and B denotes a cyano group, a benzoyl group or a phenyl sulphonyl group, or A stands for a group of the formula

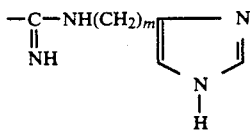

in which m has the value 2 or 3; and n stands for an integer with a value from 1 to 6, and to the physiologically acceptable salts thereof.

In the general formula 1, $R^1$ denotes a hydrogen atom or a straight chained or branched $C_1$ to $C_4$ alkyl group. Examples of such straight chained or branched $C_1$ to $C_4$ alkyl groups are the methyl, ethyl, n-propyl, isopropyl, n-butyl and sec-butyl group, the methyl group being preferred. $R^2$ stands for a hydrogen atom, a straight chained or branched $C_1$ to $C_4$ alkyl group as defined above with reference to $R^1$, a $C_1$ to $C_4$ alkoxy group, for example a methoxy, ethoxy, n-propoxy, isopropoxy or n-butoxy group, a hydroxy group, a halogen atom, for example a fluorine, chlorine or bromine atom, an amino group or a nitro group. When $R^2$ stands for a halogen atom, it is preferably a chlorine atom. Compounds in which $R^2$ is a hydrogen atom are particularly preferred.

A stands for a hydrogen atom or for a group of the formula

wherein $R^3$ denotes a hydrogen atom, an optionally substituted $C_1$ to $C_4$ alkyl group, for example a methyl, ethyl, n-propyl, isopropyl or n-butyl group, or a $C_1$ to $C_4$ alkoxy group. If the $C_1$ to $C_4$ alkyl group is substituted, it is preferably mono- or disubstituted with a halogen atom, e.g. a chlorine, bromine or iodine atom, or with a $C_1$ to $C_4$ alkoxy group, for example an ethoxy or methoxy group, and/or an aryl group, preferably a phenyl group, but an unsubstituted $C_1$ to $C_4$ alkyl group is particularly preferred, especially the methyl group.

The symbol A may also stand for a group of the formula

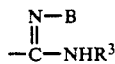

in which $R^3$ has the same meaning as defined above and B stands for a cyano group, a benzoyl group or a phenyl sulphonyl group, preferably a cyano group.

The symbol A may also stand for a group of the formula

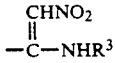

wherein $R^3$ again has the meanings defined above.

Lastly, A may stand for a group of the formula

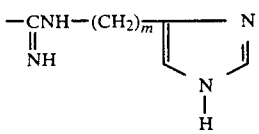

wherein m has the value 2 or 3, preferably the value 3.

The symbol n in all cases stands for an integer with a value from 1 to 6, preferably 2, 3 or 4. Compounds in which n has the value 3 are particularly preferred.

One preferred group of compounds according to the invention is characterized in that $R^1$ in the general formula I stands for a hydrogen atom or a straight chained or branched $C_1$ to $C_4$ alkyl group, in particular a methyl group, $R^2$ and A each stand for a hydrogen atom and n stands for an integer with a value from 1 to 6, in particular the number 3.

Another preferred group of compounds according to the present invention is characterized in that in the general formula I, $R^1$ stands for a hydrogen atom or a straight chained or branched $C_1$ to $C_4$ alkyl group, in particular a methyl group, $R^2$ stands for a hydrogen atom, A stands for a group of the formula

wherein $R^3$ denotes a hydrogen atom, an optionally substituted $C_1$ to $C_4$ alkyl group or a $C_1$ to $C_4$ alkoxy group and n represents an integer with a value from 1 to 6, in particular 3.

Yet another preferred group of compounds according to the present invention is characterized in that in the general formula I, $R^1$ stands for a hydrogen atom or a straight chained or branched $C_1$ to $C_4$ alkyl group, in particular a methyl group, $R^2$ stands for a hydrogen atom, A denotes a group of the formula

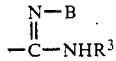

wherein $R^3$ denotes a hydrogen atom or an optionally substituted $C_1$ to $C_4$ alkyl group and B denotes a cyano group, a benzoyl group or a phenyl sulphonyl group, and n represents an integer with a value from 1 to 6, in particular 3.

Another preferred group of compounds according to the present invention is characterized in that $R^1$ stands for a hydrogen atom or a straight chained or branched $C_1$ to $C_4$ alkyl group, in particular a methyl group, $R^2$ stands for a hydrogen atom, A denotes a group of the formula

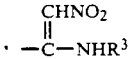

wherein $R^3$ stands for a hydrogen atom or an optionally substituted $C_1$ to $C_4$ alkyl group, and n represents an integer with a value from 1 to 6, preferably 3.

Lastly, another preferred group of the compounds according to the present invention is characterized in that in the general formula I, $R^1$ stands for a hydrogen atom or a straight chained or branched $C_1$ to $C_4$ alkyl group, in particular a methyl group, $R^2$ denotes a hydrogen atom, A stands for a group of the formula

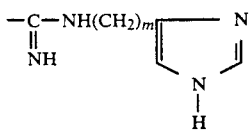

in which m has the value 2 or 3, and n represents an integer with a value from 1 to 6, in particular 3.

The following are specific examples of preferred compounds: 6-2-(3-aminopropyl)-1H-benzimidazol-5-yl]-4,5-dihydro-5-methyl-3(2H)-pyridazinone; $N^1$-[3-(imidazol-4-yl)propyl]-$N^2$-[3-[5-(4-methyl-6-oxo-1,4,5,6-tetrahydropyridazin-3-yl)-1H-benzimidazol -2-yl]propyl]-guanidine; 6-2-(2-aminoethyl)-1H-benzimidazol -5-yl]-4,5-dihydro-5-methyl-3(2H)-pyridazinone; $N^1$-[3-(imidazol-4-yl)propyl]-$N^2$-[2-[5-(4-methyl-6-oxo-1,4,5,6-tetrahydropyridazin-3-yl)-1H-benzimidazol-2-yl]ethyl]guanidine; 6-2-(4-aminobutyl)-1H-benzimidazol-5-yl]-4,5-dihydro -5-methyl-3(2H)-pyridazinone and $N^1$-[3-(imidazol-4-yl) propyl]-$N^2$-[4-5-(4-methyl-6-oxo-1,4,5,6-tetrahydropyridazin -3-yl)-1H-benzimidazol-2-yl]butyl]-guanidine and their physiologically acceptable salts.

The compounds according to the invention are prepared by a process which is characterized in that
a) for the preparation of compounds corresponding to the general formula I in which $R^1$, $R^2$ and n have the meanings defined above and A stands for a hydrogen atom,
 a$_1$) the phthalimide group is split off from a phthalimide compound corresponding to the general formula II

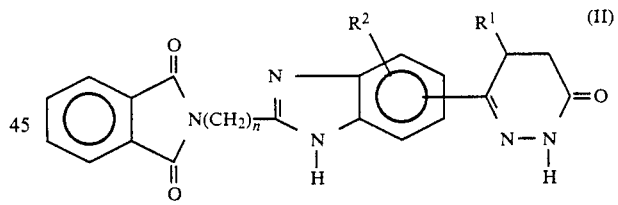

wherein $R^1$, $R^2$ and n have the meanings defined above by means of hydrazine or a chemical equivalent thereof or an aliphatic primary amine or an acid to form a compound corresponding to the general formula I, or
 a$_2$) a compound corresponding to the general formula I

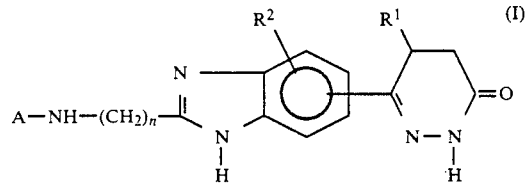

wherein $R^1$, $R^2$ and n have the meanings defined above and A stands for a group of the formula

wherein R³ has the meanings defined above is subjected to acid or basic hydrolysis;

b) for the preparation of compounds corresponding to the general formula I in which R¹, R² and n have the meanings defined above and A stands for a group of the formula

wherein R³ has the meanings defined above, a compound corresponding to the general formula Ia

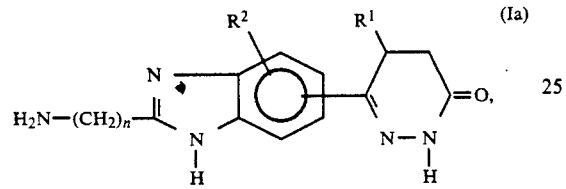

wherein R¹, R² and n have the meanings indicated above and A stands for a hydrogen atom, is reacted with an acylating agent corresponding to the general formula III

 (III)

in which R³ has the meanings indicated above and Y stands for a halogen atom, in particular a chlorine or bromine atom, a group of the formula

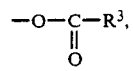

the residue of an azole or benzazole which is attached through a nitrogen atom and has at least 2 nitrogen atoms in the five membered ring, or for the group OH to form a compound corresponding to the general formula I; or c) for the preparation of compounds corresponding to the general formula 1 in which R¹, R² and n have the meanings defined above and A stands for a group of the formula

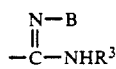

wherein R³ and B have the meanings defined above, c₁) a compound corresponding to the general formula Ia

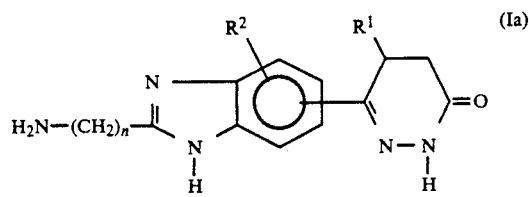

wherein R¹, R² and n have the meanings indicated above is reacted with a compound corresponding to the general formula IV

 (IV)

in which B and R³ have the meanings defined above and L stands for a removable group, for example an alkylthio, arylthio, alkoxy or aryloxy group, to form a compound corresponding to the general formula I, or c₂) a compound corresponding to the general formula Ia

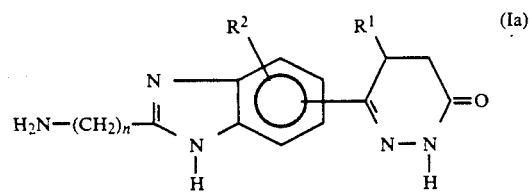

in which R¹, R² and n have the meanings indicated above is first reacted with a compound corresponding to the general formula V

 (V)

wherein B and L have the meanings indicated above to form a compound corresponding to the general formula XIII

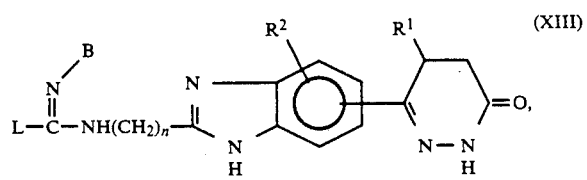

wherein R¹, R², B, L and n have the meanings indicated above, and this compound is then reacted with a compound corresponding to the general formula VI

R³-NH₂ (VI)

in which R³ has the meanings defined above to form a compound corresponding to the general formula I; or d) for the preparation of compounds corresponding to the general formula 1 in which R¹, R² and n have the meanings defined above and A stands for a group of the formula

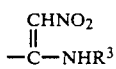

wherein R³ has the meaning indicated above, d₁) a compound corresponding to the general formula Ia

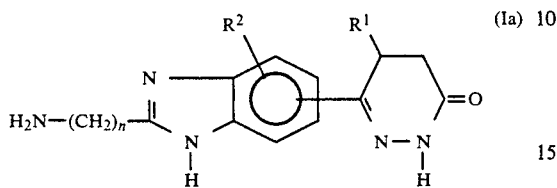

wherein R¹, R² and n have the meanings indicated above is reacted with a compound corresponding to the general formula VII

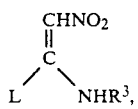

wherein L represents a removable group, for example an alkylthio, arylthio, alkoxy or aryloxy group, and R³ has the meaning indicated above, to form a compound corresponding to the general formula I, or d₂) a compound corresponding to the general formula Ia

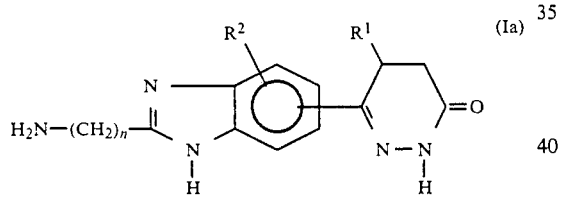

wherein R¹, R² and n have the meanings indicated above is first reacted with a compound corresponding to the general formula VIII

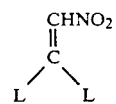

wherein L has the meaning indicated above to form a compound corresponding to the general formula IX

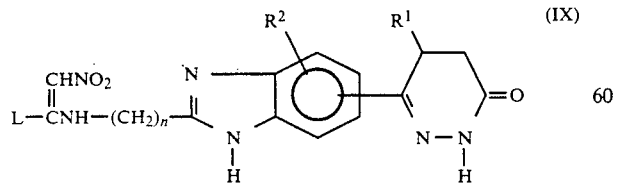

wherein R¹, R², n and L have the meanings defined above and this compound is then reacted with a compound corresponding to the general formula VI

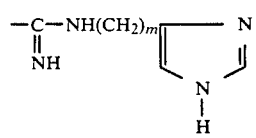

in which R³ has the meaning defined above to form a compound corresponding to the general formula I; or e) for the preparation of compounds corresponding to the general formula I in which R¹, R² and n have the meanings defined above and A stands for a group of the formula

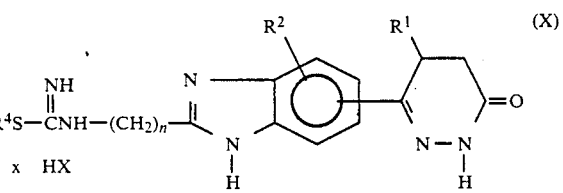

in which m has the value 2 or 3, e₁) a compound corresponding to the general formula X

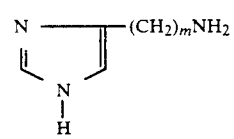

wherein R¹, R² and n have the meanings defined above, R⁴ stands for an optionally substituted C₁ to C₄ alkyl group or a benzyl group and X denotes a halogen atom or a group of the formula —OSO₂—OR⁴ is reacted with a m-(imidazol-4-yl)alkylamine corresponding to the general formula XI

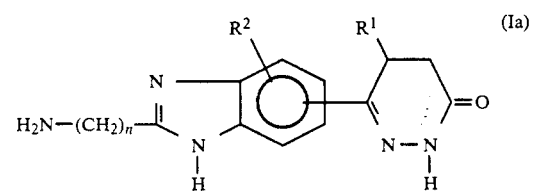

wherein m has the value 2 or 3 to form a compound corresponding to the general formula I, or e₂) a compound corresponding to the general formula Ia wherein R¹, R² and n have the meanings indicated above is reacted with a compound corresponding to the general formula XII

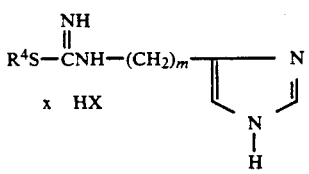
(XII)

wherein m, $R^4$ and X have the meanings defined above to form a compound corresponding to the general formula I and the compounds corresponding to the general formula 1 obtained by process variations a) to e) are optionally converted into a physiologically acceptable salt in known manner.

The compounds according to the invention corresponding to the general formula I may be prepared by several different process variations as follows:

1) compounds corresponding to the general formula I in which $R^1$, $R^2$ and n have the meanings indicated above and A stands for a hydrogen atom are obtained 1a) by the reaction of a compound corresponding to the general formula II

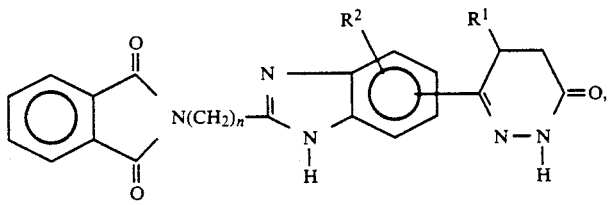
(II)

wherein $R^1$, $R^2$ and n have the meanings defined above, with hydrazine or a chemical equivalent thereof, a primary aliphatic amine or an acid. The compounds corresponding to the general formula II may be prepared, for example, by the reactions described in DE-OS 28 37 161 or by analogous reactions. By "chemical equivalents of hydrazine" are meant hydrazine hydrate, hydrazine ethanolate and similar solvates or their salts. The reactions with hydrazine or an amine such as methylamine or ethanolamine are preferably carried out with an excess of reagent in a polar solvent, for example in an alcohol such as methanol, ethanol or isopropanol. The reactions are carried out at temperatures from room temperature to the boiling point of the solvent used, preferably at the reflux temperature, and when amines are used the reactions may be carried out at an elevated pressure. Acid hydrolysis of the compounds of general formula II is carried out in aqueous mineral acids such as hydrochloric, hydrobromic or hydriodic acid, sulfuric acid or phosphoric acid or in dilute organic acids such as acetic acid or in mixtures of aqueous mineral acids and organic acids at elevated temperatures, preferably at the reflux temperature. In this reaction, the phthalimide group is split off from the compound of general formula II and the compound of general formula I is thereby obtained.

An alternative method consists of 1b) acid or basic hydrolysis of a compound corresponding to the general formula I in which $R^1$, $R^2$ and n have the meanings, defined above and A stands for the group

wherein $R^3$ has the meanings defined above. Acid hydrolysis is carried out in aqueous mineral acids such as hydrochloric or hydrobromic acid or sulfuric acid, preferably hydrochloric acid, and at elevated temperatures, preferably the reflux temperature. Basic hydrolysis is carried out in dilute solutions of alkali metal or alkaline earth metal carbonates or alkali metal or alkaline earth metal hydroxides in water, lower alcohols or mixtures of the two and at temperatures which may range from room temperature to the reflux temperature of the solvent used.

2) Compounds corresponding to the general formula I in which $R^1$, $R^2$ and n have the meanings defined above and A stands for a group of formula

wherein $R^3$ has the meanings defined above are obtained by the reaction of a compound of the general formula Ia in which $R^1$, $R^2$ and n have the meanings indicated above and A stands for a hydrogen atom with an acylating agent corresponding to the general formula III $$R^3-\overset{\overset{O}{\|}}{C}-Y$$
(III)

wherein $R^3$ has the meanings indicated above and Y stands for a halogen atom, in particular a chlorine or bromine atom, the group

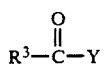

in which $R^3$ has the meanings indicated above, the residue of an azole or benzazole which has at least 2 nitrogen atoms in the five membered ring and is attached through a nitrogen atom, or the group OH. Examples of the above mentioned azoles and benzazoles include the imidazole, 1,2,4-triazole, tetrazole, benzimidazole and benzotriazole ring. If the acylating agent used is a compound of the general formula III in which Y stands for the group OH then it is advisable to add an activating agent which serves to increase the acylating potential of the carboxylic acid. Activating agents used for this purpose may be dehydrating or water binding agents such as carbodiimides or they may be agents which convert the carboxylic acids into the corresponding acid halides, anhydrides, mixed carboxylic acid/carbonic acid anhydrides or azolides which function as acylating agents. Examples of the latter type of activating agent include phosgene, chloroformates N,N'-carbonyl-diimidazole. The reaction between the acylating agent corresponding to the general formula III and the compound corresponding to the general formula I in which $R^1$, $R^2$ and n have the meanings indicated above and A stands for a hydrogen atom is advantageously carried out in an inert solvent such as a halogenated hydrocarbon, ether, pyridine, dimethyl formamide or an aromatic hydrocarbon at temperatures from $-20°$ C. to the boiling point of the solvent used. The molar ratio of acylating agent of formula III to the compound of general formula 1 is normally in the range of 3:1 to 1:1, preferably from 2:1 to 1:1. If an acid is split off in the acylating reaction, it is advantageous to add an acid acceptor such as, for example, a tertiary amine such as triethylamine or pyridine.

3) Compounds corresponding to the general formula I in which $R^1$, $R^2$ and n have the meanings defined above and A stands for a group of the formula

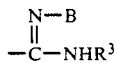

wherein $R^3$ and B have the meanings defined above may be obtained by two different process variations:

According to one variation (3a), a compound of the general formula Ia in which $R^1$, $R^2$ and n have the meanings indicated above is reacted with a compound corresponding to the general formula IV

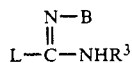 (IV)

wherein B and $R^3$ have the meanings defined above and L stands for a removable group such as, for example, an alkylthio, arylthio, alkoxy or aryloxy group. The phenoxy and methylthio group are preferred removable groups. The reaction is preferably carried out with equimolar quantities of the reactants in the presence of a solvent and at elevated temperatures, preferably at the reflux temperature of the solvent used.

According to the second process variation (3b), the compound corresponding to the general formula Ia in which $R^1$, $R^2$ and n have the meanings indicated above is reacted in a two stage process, first with a compound corresponding to the general formula V

 (V)

in which B and L have the meanings indicated above.

This stage results in the formation of an intermediate compound corresponding to the above formula XIII in which $R^1$, $R^2$, B, L and n have the meanings already indicated. This compound is then reacted with a compound corresponding to the general formula VI

$R^3—NH_2$ (VI)

in which $R^3$ has the meanings defined above.

In the first stage of this process variation, the components are reacted together in equimolar quantities in an inert, aprotic solvent, for example an ether such as tetrahydrofuran or solvents such as acetonitrile, dimethyl formamide or dimethyl sulphoxide. The reaction may in principle be carried out at temperatures from $-20°$ C. to the reflux temperature of the solvent used but is preferably carried out at temperatures from $10°$ to $30°$ C.

Concerning the solvents and reaction temperature for the second stage, the reaction conditions to be employed are the same as those mentioned for process variation 3a. The amine corresponding to the general formula VI is preferably used in a large excess, particularly a 5 to 10 times excess.

The intermediate compound corresponding to the general formula XIII

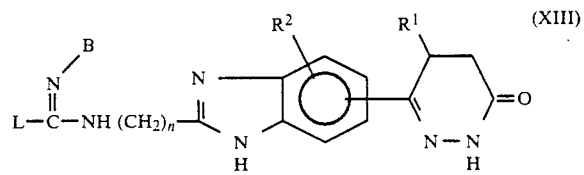 (XIII)

in which $R^1$, $R^2$, B, L and n have the meanings defined above may be isolated by conventional methods but is preferably reacted directly with the amine of formula VI without isolation or purification.

4) Compounds corresponding to general formula I in which $R^1$, $R^2$ and n have the meanings defined above and A stands for a group of the formula

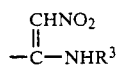

in which $R^3$ has the meanings indicated above may be obtained by two different process variations:

According to one variation (4a), a compound corresponding to the general formula Ia in which $R^1$, $R^2$ and n have the meanings indicated above is reacted with a compound corresponding to the general formula VII

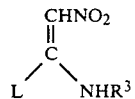 (VII)

in which L and $R^3$ have the meanings defined above to form a compound corresponding to the general formula I.

According to the other process variation (4b), a compound corresponding to the general formula Ia in which $R^1$, $R^2$ and n have the meanings defined above is first reacted with a compound corresponding to the general formula VIII

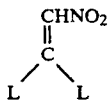

in which L has the meaning defined above to form an intermediate compound corresponding to the above general formula IX in which $R^1$, $R^2$, L and n have the meanings defined above. This intermediate compound is then reacted with a compound corresponding to the general formula VI $$R^3\text{-}NH_2 \qquad (VI)$$

in which $R^3$ has the meanings defined above to form a compound corresponding to the general formula I.

In both process variations, the removable group L in compounds corresponding to formulae VII and VIII is preferably an alkylthio group, in particular the methylthio group. The compounds of formulae VII and VIII are preferably used in equimolar quantities, based on the compounds of formula Ia. The reactions are carried out in polar solvents such as acetonitrile, pyridine, dimethyl formamide or alcohols, preferably secondary or tertiary alcohols, e.g. isopropanol, and at an elevated temperature, in particular at the reflux temperature. In the second stage of the two stage process, the intermediate compound corresponding to the general formula IX is reacted with a large excess of the amine of formula VI, preferably a 10 to 30 times excess, in a solvent, the choice of which is not critical for the outcome of the reaction, and at an elevated temperature, preferably at the reflux temperature of the solvent used.

5) Compounds corresponding to the general formula I in which $R^1$, $R^2$ and n have the meanings defined above and A stands for a group of the formula

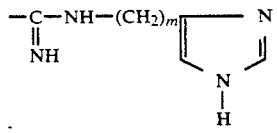

in which m has the value 2 or 3 are obtained 5a) by the reaction of a compound corresponding to the general formula X

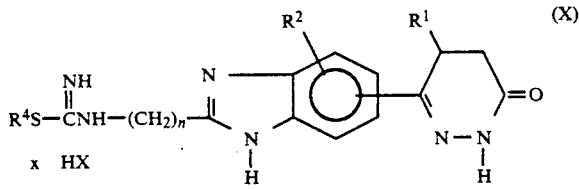

in which $R^1$, $R^2$ and n have the meanings defined above, $R^4$ stands for an optionally substituted $C_1$ to $C_4$ alkyl group (which alkyl group may be, for example, mono- or disubstituted with a halogen atom, for example a chlorine, bromine or iodine atom, a $C_1$ to $C_4$ alkoxy group. For example a methoxy or ethoxy group, and/or an aryl group, in particular a phenyl group) or it stands for a benzyl group and X denotes a halogen atom or a group of the formula $-OSO_2OR^4$ (wherein $R^4$ has the meaning already indicated) with a m-(imidazol-4-yl)alkylamine corresponding to the general formula XI

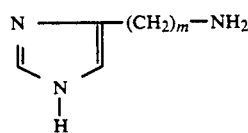

in which m has the value 2 or 3, or 5b) by the reaction of a compound corresponding to the general formula Ia in which $R^1$, $R^2$ and n have the meanings defined above with a compound corresponding to the general formula XII

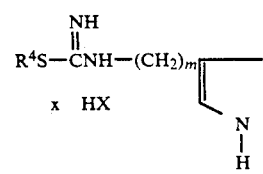

wherein $R^4$, X and m have the meanings defined above.

The reactants are preferably reacted together in equimolar quantities in a polar, aprotic solvent such as pyridine, dimethyl formamide, dimethyl sulphoxide or acetonitrile and at an elevated temperature, in particular at the reflux temperature of the solvent used.

The compounds obtained by the different process variations are isolated and purified in conventional manner, for example by recrystallization, chromatographic procedures etc.

The compounds obtained by the different process variations may optionally be converted into their physiologically acceptable salts. These salts may be obtained, for example, by a reaction with mineral acids such as hydrochloric, hydrobromic hydriodic acid, phosphoric acid, metaphosphoric acid, nitric acid or sulfuric acid or with organic acids such as formic acid, acetic acid, propionic acid, phenyl acetic acid, tartaric acid, citric acid, fumaric acid, methane sulphonic acid, embonic acid, etc.

The compounds according to the invention corresponding to the general formula I may be present as a series of tautomeric forms or in several stereoisomeric forms. This invention therefore covers not only the salts and hydrates of the compounds of general formula 1 described above but also all tautomeric and stereoisomeric forms.

The compounds according to the invention may be formulated in any desired manner for administration. The invention therefore also covers pharmaceutical preparations containing at least one compound according to the invention for use in human of veterinary medicine. Such pharmaceutical preparations may be conventionally prepared with the aid of one or more pharmaceutically acceptable carriers or diluents.

The compounds according to the invention may therefore be formulated for oral, buccal, topical, parenteral or rectal administration.

For oral administration, the pharmaceutical preparation may be in the form of, for example, tablets, capsules, powders, solutions, syrups or suspensions prepared by the conventional methods with the aid of acceptable diluents.

For buccal administration, the pharmaceutical preparation may be in the form of tablets or sachets formulated in the conventional manner.

The compounds according to the invention may be formulated for parenteral administration by bolus injection or continuous infusion. Formulations for injection may be prepared in single dose form as ampoules or in multiple dose containers with added preservative.

The pharmaceutical preparations may assume forms such as suspensions, solutions or emulsions in oily or aqueous carriers and they may contain formulating auxiliaries such as stabilizers and/or suspending or dispersing agents.

Alternatively, the active ingredient may be present in powder form to be reconstituted with a suitable carrier such as sterile, pyrogen free water before use.

The compounds according to the invention may also be formulated as rectal preparations, for example suppositories or retention enemas, which may contain, for example, conventional suppository excipients such as cocoa butter or other glycerides.

For topical application, the compounds according to the invention may be formulated in the conventional manner as ointments, creams, gels, lotions, powders or sprays.

For oral administration, a suitable daily dose of compounds according to the invention may be divided into one to four doses with a total of from 5 mg to 1 g per day, depending on the condition of the patient. In some cases it may be necessary to deviate from the quantities mentioned above, depending on the individual response to the active ingredient or the nature of its formulation and the time or time interval of administration. In some cases, it may be sufficient to use less than the minimum quantity stated above while in other cases it may be necessary to exceed the upper limit.

The benzimidazoles according to the invention corresponding to the general formula 1 combine good oral availability with interesting pharmacological properties, especially cardiovascular effects, in particular positive inotropic and blood pressure lowering effects. They show an excellent cardiotonic activity in numerous pharmacological standard models, for example in vitro in the isolated, perfused Langendorff heart or in vivo on narcotized guinea pigs, where they produce a marked increase in contractility.

1. Investigations on isolated, perfused Langendorff Hearts (guinea pigs)

a) Method

The arrangement of Langendorff was modified according to P. R. Beckett (J. Pharm. Pharmacol. 22, 818 (1970)) and R. M. Abel and R. L. Reis (Circ. Res. 27, 961,(1970)) to determine the haemodynamic effects of the compounds according to the invention on isolated, perfused guinea pig hearts. The spontaneously beating guinea pig hearts were catheterized in the left ventricle and perfused with solutions of the test substances in physiological saline solution/ethanol (9:1) at concentrations of $10^{-4}$ to $10^{-8}$ mol/l at a constant perfusion pressure of 60 mm Hg.

b) Measured Values

| Example Number | Concentration range (mol/l) | Maximum percentage changes compared with controls | | |
|---|---|---|---|---|
| | | Contractility dp/dt | Coronary Flow | Cardiac Frequency |
| 1 | $10^{-8}$–$10^{-4}$ | +76% | +25% | +11% |
| 6 | $10^{-7}$–$10^{-5}$ | +161% | +52% | +20% |
| Pimobendane (Comparison) | $10^{-7}$–$10^{-5}$ | +99% | +76% | +8% |

2. Haemodynamic Characterization on Narcotized Guinea Pigs (in vivo model)

a) Method

The animals were narcotized with urethane (1 5 g/kg). The trachea was cannulated for volume controlled respiration. The two carotid arteries were then exposed operatively. A Tip catheter (3F) was introduced through the right carotid artery and moved forwards through the ascending aorta into the left ventricle while the pressure was continuously recorded. Successful passage through the aortic valves is recognized by the typical left ventricular pressure curve. A thermistor probe (3F, F. Edwards) is pushed forwards into the aortic arch through the left carotid for thermodilution. The thermistor probe also has a lumen for the recording of arterial blood pressure. A catheter is passed through the right jugular vein to be placed in front of the right auricle for application of the cold injectate (0.2 ml of 0.9% NaCl, 15° C). The ECG is recorded in the first shunt. All substances are dissolved in physiological saline solution and infused through the left jugular vein (infusion volume 0.02 ml/min). The drug is applied after haemodynamic stabilization and under $\beta$-blockage (metoprolol 2 mg/kg i.m.). All circulatory parameters are continuously registered on a direct recorder. The pulse frequency is calculated from the ECC, the contractibility (dp/dt) is calculated from the volume curve and the volumetric cardiac output per unit time is calculated from the thermodilution curve.

b) Measured Values

| Example Number | Dose (µg/kg/min) | Maximum percentage changes compared with initial values | | |
|---|---|---|---|---|
| | | Contractility dp/dt | Blood Pressure sys. | Cardiac Frequency |
| 1 | 10 | +38% | −25% | +20% |
| 6 | 10 | +97% | −15% | +17% |
| Pimobendane (Comparison) | 10 | +10% | −51% | +3% |

The inhibitory action of the compounds according to the invention on phosphodiesterase was tested on phosphodiesterase type III obtained from ox heart (Sigma Chemie, BRD) by the methods of W. Diederen and H. Weisenberger (Arzneim.-Forschung 31, 177 (1981)) (Method A) and of M. A. Appleman and W. L. Terasaki (Advances in Cyclic Nucleotide Research, volume 5, Raven Press, New York (1975), page 153) (Method B). The table shows the percentage inhibition of PDE-III activity.

| | | Concentration (mol/l) | | | |
|---|---|---|---|---|---|
| | | $10^{-7}$ | $10^{-6}$ | $10^{-5}$ | $10^{-4}$ |
| Example 1 | Method A | 0 | 0 | 7 | 10 |
| | Method B | 0 | 0 | 0 | 4 |
| Pimobendane (comparison) | Method A | 7 | 15 | 30 | — |
| | Method B | — | 5 | 19 | 57 |

EXAMPLE 1

6-[2-(3-aminopropyl)-1-benzimidazol-5-yl]-4,5-dihydro-5-methyl-3(2H)-pyridazinone

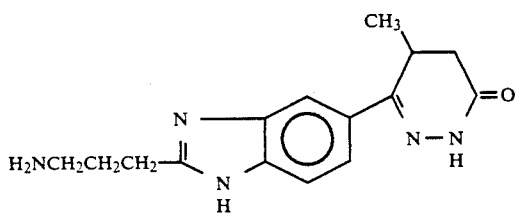

a)
6-[3-nitro-4-4-(phthalimido)butyryl]amino]phenyl]-4,5-dihydro-5-methyl-3(2H)-pyridazinone

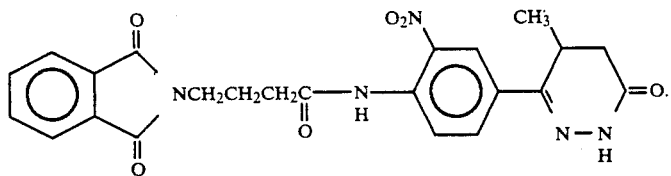

49.7 g (200 mmol) of 6-(4-amino-3-nitro-phenyl)-4,5-dihydro -5-methyl-3(2H)-pyridazinone and 52 9 g (210 mmol) of 4-phthalimido-butyric acid chloride are stirred together in 500 ml of pyridine for 4 hours at a reaction temperature of 100° C. The cooled reaction mixture is poured out on 1500 ml of ice water and the oil which separates is extracted twice with 1000 ml portions of dichloromethane. The combined organic phases are washed with 250 ml of water, dehydrated with sodium sulfate and filtered. The residue obtained after evaporation of the solvent under vacuum is recrystallized from ethyl acetate". 69.6 g (75%) of yellow crystals are obtained.

$C_{23}H_{21}N_5O_6$ (463.45).
m.p. 182°–184° C.

b)
6-[3-amino-4-[[4-(phthalimido)butyryl]amino]phenyl]-4,5-dihydro-5-methyl-3(2H)-pyridazinone

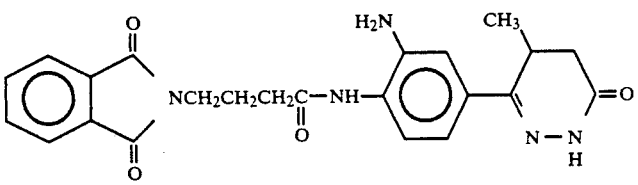

A suspension of 15.8 g (34 mmol) of 6l-[3-nitro-4-[[4-(phthalimido) butyryl]amino]phenyl]-4,5-dihydro-5-methyl-3(2H)-pyridazinone in 350 ml of ethanol is hydrogenated under a hydrogen pressure of 5 at 50° C. in the presence of 1.6 g of palladium charcoal (10% Pd). When uptake of hydrogen has been completed (about 8 hours), the solution is diluted with 350 ml of dichloromethane and filtered through a supercel layer. After evaporation under vacuum, the filtrate yields 14.1 g (96%) of a brownish yellow solid which is used for the next stage without purification.

$C_{23}H_{23}N_5O_4$ (433.47).
m.pt. 190°–191° C. (from ethanol/acetonitrile 4:1).

6-[2-(3-phthalimidopropyl)-1H-benzimidazol-5yl]-4,5-dihydro -5-methyl-3(2H)-pyridazinone

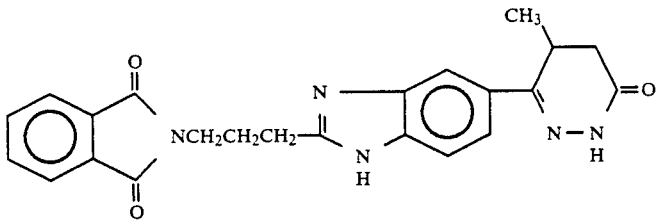

14.1 g (32.5 mmol) of 6-[3-amino-4-[[4-(phthalimido) butyryl]amino]phenyl]-4,5-dihydro-5-methyl-3(2H)-pyridazinone are boiled under reflux in 100 ml of glacial acetic acid for 2 hours. The solution is concentrated by extensive evaporation under vacuum and 200 ml of ethanol are added to the residue. After 30 minutes stirring at room temperature, the reaction mixture is cooled to 5° C. and the resulting precipitate is suction filtered. 7.7 g (57%) of a solid melting at 260° to 261° C. are obtained.

$C_{23}H_{21}N_5O_3$ (415.45).

d)
6-[2-(3-aminopropyl)-1H-benzimidazol-5-yl]-4,5-dihydro-5-methyl-3(2H) -pyridazinone 25.9 g (62 mmol) of 6-[2-(3-phthalimidopropyl)-1H-benzimidazol -5-yl]-4,5-dihydro-5-methyl-3(2H)-pyridazinone and 16.0 ml (330 mmol) of hydrazine hydrate are boiled under reflux in 300 ml of ethanol for 1 5 hours. The thick suspension obtained is concentrated by evaporation under vacuum and the residue is taken up with 500 ml of 2N hydrochloric acid and the solution is filtered. The filtrate is concentrated by evaporation under vacuum and after the addition of 100 ml of ethanol it is again concentrated by evaporation. The solid obtained as residue is taken up with 200 ml of saturated potassium carbonate solution and the mixture is extracted with 3×100 ml of isopropanol. The combined organic phases are dried and concentrated by evaporation under vacuum. 13.9 g (79%) of a colorless solid are obtained after recrystallization from ethanol/water.

$C_{15}H_{19}N_5O$ (285.35).

m p. 228.5°–229 5° C.

Monohydrochloride m.p. 209°–211° C.

Dihydrochloride m.p. 213°–217° C.

| $^1$H-NMR data (DMSO-$d_6$, TMS as internal standard) | δ = 1.1 (d) 3H |
|---|---|
| | 1.85 (s) 3H |
| | 1.7–3.0 (m) 6H |
| | 3.1–3.4 (m) 2H |
| | 3.55 (t) 1H |
| | 7.5–8.2 (m) 4H, 1H replaceable by $D_2O$ |
| | 11.0 (s) 1H replaceable by $D_2O$ |
| | 12.5 (broad) 1H replaceable by $D_2O$ ppm |

EXAMPLE 3

$N^1$-cyano-$N^2$-methyl-$N^3$-[3-5-(4-methyl-6-oxo-1,4,5,6-tetrahydropyridazin-3-yl)-1H-benzimidazol-2-yl]propyl]guanidine

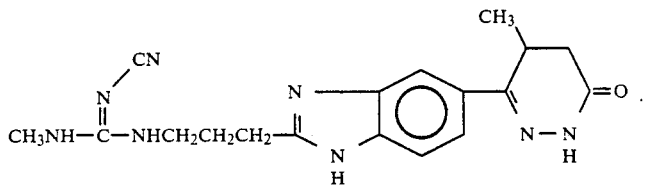

0.50 g (1.75 mmol) of 6-2-(3-aminopropyl)-1H-benzimidazol-yl]-4,5-dihydro-5-methyl-3(2H)-pyridazinone and 0.31 g (1.76 mmol) of $N^1$-cyano-$N^2$-methyl-0-phenyl-isourea are boiled under reflux in 20 ml of isopropanol for 3 hours. The reaction mixture is filtered while still hot and the filtrate is concentrated by evaporation under vacuum. The pale yellow residue is chromatographer on silica gel with dichloromethane/methanol (9:1) and yields 0.42 g (65%) of a colorless, amorphous solid after concentration of the main fraction by evaporation under vacuum.

$C_{18}H_{22}N_8O$ (366 43).

EXAMPLE 2

6-[2-(3-acetamidopropyl)-1H-benzimidazol-5-yl]-4,5-dihydro-5-methyl-3(2H)-pyridazinone

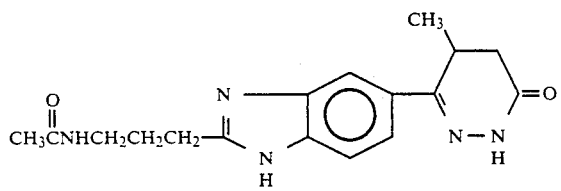

0.50 g (1 75 mmol) of 6-2-(3-aminopropyl)-1H-benzimidazol-yl]-4,5-dihydro-5-methyl-3(2H)-pyridazinone are boiled with 0.34 ml (3.50 mmol) of acetic anhydride in 20 ml of glacial acetic acid for 45 minutes. The cooled solution is extensively concentrated by evaporation under vacuum and the residue is taken up with 10 ml of water. The resulting solution is adjusted to pH 9 with 10% ammonia. After concentration of this solution by evaporation to about one-third of its volume and cooling in an ice bath, a yellowish solid crystallizes, and this solid is suction filtered and then boiled up in 30 ml of acetonitrile. The solid obtained as residue is suction filtered, washed with 10 ml of acetonitrile and dried under vacuum. 0 51 g (89%) of colorless crystals melting at 244° to 246° C. are obtained.

$C_{17}H_{21}N_5O_2$ (327 39).

| $^1$H-NMR-data (CD$_3$OD, TMS as internal standard) | δ = 1.2 (d) 3H |
|---|---|
| | 1.9–3.1 (m) 6H |
| | 2.85 (s) 3H |
| | 3.3–3.7 (m) 3H |
| | 4.9 (broad) 4H replaceable by $D_2O$ |
| | 7.6–8.0 (m) 2H |
| | 8.15 (s) 1H ppm |

EXAMPLE 4

$N^1$-cyano-$N^2$-isopropyl-$N^3$-[3-[5-(4-methyl-6-oxo-1,4,5,6-tetrahydropyridazin-3-yl)-1H-benzimidazol-2-yl]propyl]guanidine

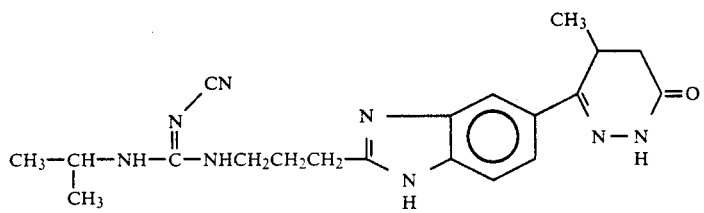

0.43 g (44%) of a colorless, amorphous solid is obtained by a method analogous to that of Example 3 from 0.70 g (2.45 mmol) of 6-[2-(3-aminopropyl)-1H-benzimidazol-5-yl]-4,5-dihydro-5-methyl-3(2H)-pyridazinone and 0.50 g (2.46 mmol) of $N^1$-cyano-$N^2$-isopropyl-0-phenyl-isourea.

$C_{20}H_{26}N_8O$ (394.48).

| $^1$H-NMR-data (DMSO-$d_6$, TMS as internal standard) | $\delta =$ 1.0–1.3 (2d) 9H<br>1.8–3.1 (m) 6H<br>3.2–3.7 (m) 3H<br>3.8–4.2 (m) 1H<br>6.9 (d) 1H replaceable by D$_2$O<br>7.3 (t) 1H replaceable by D$_2$O<br>7.6–8.2 (m) 3H<br>11.1 (s) 1H replaceable by D$_2$O<br>12.6 (broad) 1H replaceable by D$_2$O ppm |

EXAMPLE 5

1-methylamino-1-[3-[5-(4-methyl-6-oxo-1,4,5,6-tetrahydropyridazin -3-yl)-1H-benzimidazol-2-yl]propylamino]-2-nitroethene

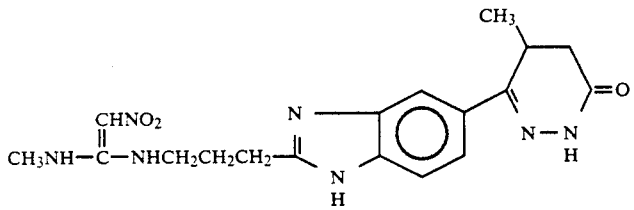

2.00 g (7 0 mmol) of 6-2-(3-aminopropyl)-1H-benzimidazol-5-yl]-4,5-dihydro-5-methyl-3(2H)-pyridazinone and 1 16 g (7 0 mmol) of 1,1-bis-(methylthio)-2-nitroethene are boiled under reflux in 50 ml of isopropanol for 1 hour. After cooling, the solution is concentrated by evaporation under vacuum and 10 ml of a solution of methylamine in methanol (11 mol/1) are added to the intermediate stage without purification of the latter. The solution is boiled under reflux for 30 minutes and then concentrated by evaporation under vacuum. The residue is recrystallized from methanol. 0 72 g (27%) of a yellow solid melting at 168° to 170° C. is obtained.

$C_{18}H_{23}N_7O_3$ (385.43).

| $^1$H-NMR data (DMSO-$d_6$, TMS as internal standard) | $\delta =$ 1.1 (d) 3H<br>1.9–3.1 (m) 9H<br>3.2–3.7 (m) 3H<br>6.7 (s) 1H<br>7.6–8.2 (m) 3H<br>10.3 (broad) 2H replaceable by D$_2$O<br>11.1 (s) 1H replaceable by D$_2$O<br>12.6 (broad) 1H replaceable by D$_2$O |

EXAMPLE 6

$N^1$-3-(imidazol-4-yl)propyl]-$N^2$-[3-5-(4-methyl-6-oxo-1,4,5,6-tetrahydropyridazin-3-yl)-1H-benzimidazol-2-yl]propyl]guanidine

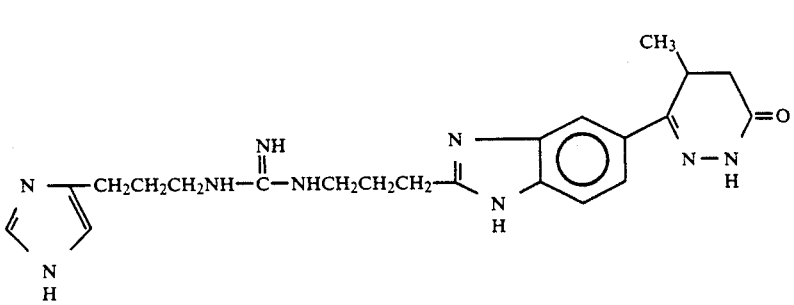

0 77 g (1 58 mmol) of N-[3-5-(4-methyl-6-oxo-1,4,5,6-tetrahydropyridazin -3-yl)-1H-benzimidazol-2-yl]propyl]-S-methylisothiuronium iodide and 0 20 g (1 59 mmol) of 3-(imidazol-4-yl)propylamine are boiled under reflux in 30 ml of pyridine for 3.5 hours. The cooled solution is concentrated by evaporation under vacuum and the residue is chromatographed on silica gel using, as eluting solvent, ethyl acetate/methanol/conc. ammonia saturated with ammonium chloride (50: 47.5:2 5). The main fraction (Rf value 0.39) is concentrated by evaporation under vacuum, the residue obtained is taken up with 10 ml of saturated potassium carbonate solution and the aqueous phase is extracted three times with 20 ml of isopropanol. The organic phase is dried, filtered and concentrated by evaporation under vacuum. 0.32 g (47%) of a colorless, amorphous solid is left behind.

$C_{22}H_{29}N_9O$ (435 53).

| $^1$H-NMR data (CD$_3$OD, TMS as internal standard) | $\delta =$ 1.2 (d) 3H<br>1.7–3.7 (m) 15H<br>5.2 (broad 6H replaceable by D$_2$O<br>6.95 (s) 1H<br>7.4–8.2 (m) 4H ppm |

EXAMPLE 7

N[1]-cyano-N[2]-[3-[5-(4-methyl-6-oxo-1,4,5,6-tetrahydropyridazin-3-yl)
-1H-benzimidazol-2-yl]propyl]guanidine

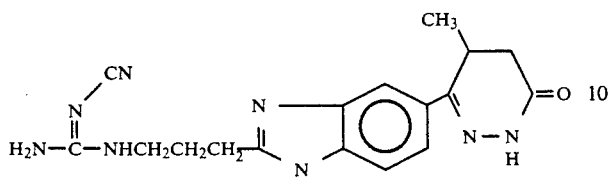

0.31 g (50% of a yellow, amorphous solid is obtained by a method analogous to that of Example 3 from 0.50 g (1.75 mmol) of 6-[2-(3-aminopropyl)-1H-benzimidazol-5yl]-4,5-dihydro-5methyl-3(2H)-pyridazinone and 0.30 g (1.86 mmol) of N-cyano-0-phenylisourea after chromatographic purification on silica gel with ethyl acetate/ethanol/ammonia (70:30:2) as eluent $C_{17}H_{20}N_8O$ (352.40).

| 1H-NMR data (CD3OD, TMS as internal standard) | $\delta$ = | 1.2 (d) 3H<br>1.9–2.3 (m) 2H<br>2.5–3.7 (m) 7H<br>4.9 (broad) 5H replaceable by D$_2$O<br>7.6–8.2 (m) 3H ppm |
|---|---|---|

EXAMPLE 8

N[1]-benzoyl-N[2]-methyl-N[3]-[3-[5-(4-methyl-6-oxo-1,4,5,6-tetrahydropyridazin
-3-yl)-1H-benzimidazol-2-yl]propyl]guanidine

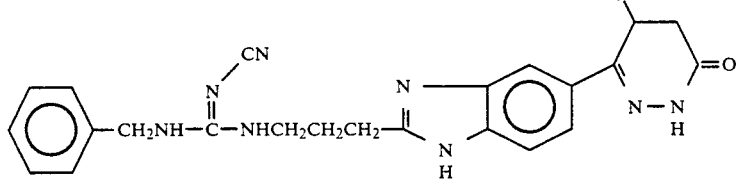

0.44 g (1.54 mmol) of 6-[2-(3-aminopropyl)-1H-benzimidazol-5-yl]-4,5-dihydro-5-methyl-3(2H)-pyridazinone and 0.43 g.(1.71 mmol) of N[1]-benzyl-N[2]-cyano-0-phenyl-isourea are boiled under reflux in 20 ml of isopropanol for 4 hours. The solid obtained after cooling of the solution to room temperature is suction filtered and recrystallized from methanol. 0.28 g (41%) of colorless crystals melting at 270° C. are obtained.
$C_{24}H_{26}N_8O$ (L442.52).

| 1H-NMR data (DMSO-d$_6$, TMS as internal standard) | $\delta$ = | 1.1 (d) 3H<br>1.9–2.2 (m) 2H |
|---|---|---|

| | 2.3–3.1 (m) 4H<br>3.2–3.6 (m) 3H<br>4.5 (d) 2H<br>7.3–8.0 (m) 9H, 1H replaceable by D$_2$O<br>8.1 (t) 1H replaceable by D$_2$O<br>11.0 (s) 1H replaceable by D$_2$O ppm |
|---|---|

EXAMPLE 9

N[1]-benzoyl-N[2]-methyl-N[3]-[3-[5-(4-methyl-6-oxo-1,4,5,6-tetrahydropyridazin-3-yl)-1H-benzimidazol-2-yl]propyl]guanidine

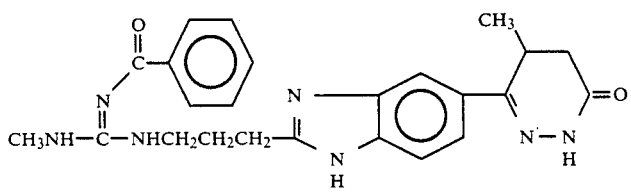

a)
N[1]-benzoyl-N[2]-[3-[5-(4-methyl-6-oxo-1,4,5,6-tetrahydropyridazin
-3-yl)-1H-benzimidazol-2-yl]propyl]-0-phenyl-isourea 0.50 g (1.75 mmol) of 6-[2-(3-aminopropyl)-1H-benzimidazol -5-yl]-4,5-dihydro-5-methyl-3(2H)-pyridazinone and 0 56 g (1 76 mmol) of N-benzoyldiphenylimidocarbonate in 20 ml of isopropanol are stirred at room temperature for 3 hours. The solid which precipitates is suction filtered, washed with a small quantity of cold isopropanol and dried under vacuum. 0.70 g (79%) of a colorless solid melting at 125° C. are obtained.
$C_{29}H_{28}N_6O_3$ (508.58).

b)
N[1]-benzoyl-N[2]-methyl-N[3]-[3-[5-(4-methyl-6-oxo-1,4,5,6-tetrahydropyridazin
-3-yl)-1H-benzimidazol-2-yl]propyl]guanidine.

1.5 ml (16.5 mmol) of a solution of methylamine in methanol (11 mol/1) are added to 0 63 g (1 23 mmol) of N[1]-benzoyl-N[2]-[3-[5-(4-methyl-6-oxo-1,4,5,6-tetrahydropyridazin -3-yl)-1H-benzimidazol-2-yl]propyl]-0-phenylisourea in 20 ml of methanol and the reaction mixture is stirred for 4 hours. The yellowish oil obtained after removal of the solvent by evaporation under vacuum is chromatographed on silica gel with dichloromethane/methanol (9:1) as solvent and yields 0.48 g (87%) of a colorless, amorphous solid after concentration of the main fraction by evaporation.
$C_{24}H_{27}N_7O_2$ (445.52).

| $^1$H-NMR data (DMSO-$d_6$, TMS as internal standard) | δ = 1.15 (d) 3H<br>2.0–3.2 (m) 6H<br>2.95 (s) 3H<br>3.3–3.7 (m) 3H<br>5.0 (broad) 4H replaceable by $D_2O$<br>7.3–8.3 (m) 8H ppm |
|---|---|

EXAMPLE 10

N$^1$-methyl-N$^2$-[3-[5-(4-methyl-6-oxo-1,4,5,6-tetrahydropyridazin-3-yl)-1H-benzimidazol-2-yl]propyl]-N$^3$-phenylsulphonylguanidine

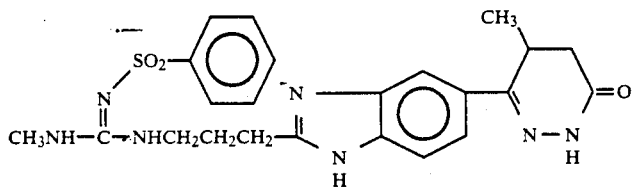

a)
S-methyl-N$^1$-[3-5-(4-methyl-6-oxo-1,4,5,6-tetrahydropyridazin-3-yl)-1H-benzimidazol-2-yl]propyl]-N$^2$-phenylsulphonyl-isothiourea.

0.50 g (1 75 mmol) of 6-[2-(3-aminopropyl)-1H-benzimidazol-5-yl]-4,5-dihydro-5-methyl-3(2H)-pyridazinone and 0.56 g (1.75 mmol) of N-phenylsulphonyl-imino-dithio-carbonic acid dimethyl ester in 20 ml of isopropanol are stirred for 9 hours at 50° C. The solvent is evaporated off under vacuum and the oily residue is chromatographed on silica gel with dichloromethane/methanol (9:1) as solvent. After concentration of the main fraction by evaporation under vacuum, 0.85 g (97%) of a yellowish, amorphous solid are obtained.
$C_{23}H_{26}N_6O_3S_2$ (498.62).

| $^1$H-NMR data (CDCl$_3$, TMS as internal standard) | δ = 1.2 (d) 3H<br>2.0–2.7 (m) 4H<br>2.3 (s) 3H<br>2.8–3.1 (m) 2H<br>3.2–3.6 (m) 3H<br>7.4–8.2 (m) 8H<br>8.5 (broad) 1H replaceable by $D_2O$<br>10.1 (broad) 1H replaceable by $D_2O$ ppm |
|---|---| b)
N$^1$-methyl-N$^2$-[3-5-(4-methyl-6-oxo-1,4,5,6-tetrahydropyridazin-3-yl)-1H-benzimidazol-2-yl]propyl]-N$^3$-phenylsulphonyl-guanidine.

0.85 g (1 7 mmol) of S-methyl-N$^1$-[3-5-(4-methyl-6-oxo-1,4,5,6-tetrahydropyridazin-3-yl)-1H-benzimidazol-2-yl]propyl]-N$^2$-phenylsulphonyl-isothiourea in 20 ml of ethanol are stirred together with 1 7 ml (17 mmol) of a solution of methylamine in methanol (10 mol/1) at room temperature. After 20 hours, the solid which precipitates is suction filtered, washed with ethanol and boiled up with 30 ml of methanol. The solid obtained after suction filtration is dried under vacuum. 0.65 g (79%) of a colorless solid melting at 258° to 260° C. are obtained.
$C_{23}H_{27}N_7O_3S$ (481 57).

| $^1$H-NMR data (DMSO-$d_6$, TMS as internal standard) | δ = 1.15 (d) 3H<br>1.9–3.1 (m) 6H<br>2.8 (d) 3H<br>3.2–3.7 (m) 3H<br>7.3–8.1 (m) 10H, 2H replaceable by $D_2O$<br>11.1 (s) 1H replaceable by $D_2O$ ppm |
|---|---|

EXAMPLE 11

6-2-(2-aminoethyl)-1H-benzimidazol-5-yl]-4,5-dihydro-5-methyl -3(2H)-pyridazinone

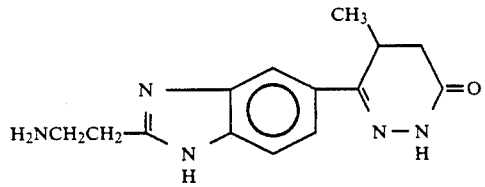

Prepared by a method analogous to that of Example 1d) from 1.44 g (3 6 mmol) of 6-[2-(2-phthalimidoethyl)-1H-benzimidazol-5-yl]-4,5-dihydro-5-methyl-3(2H)-pyridazinone and 0.9 ml (18 mmol) of hydrazine hydrate. The crude product is chromatographed on silica gel with methanol/conc. ammonia (99:1). After concentration of the main fraction by evaporation under vacuum and crystallization of the residue from ethanol, 0 55 g (51%) of a colorless solid melting at 178° C. are obtained.
$C_{14}H_{17}N_5O$ (271.32).

| $^1$H-NMR data (CD$_3$OD, TMS as internal standard) | δ = 1.2 (d) 3H<br>2.2–2.9 (m) 2H<br>3.1–3.3 (m) 4H<br>3.3–3.7 (m) 1H<br>5.4 (broad) 4H replaceable by $D_2O$<br>7.6–8.2 (m) 3H ppm |
|---|---|

EXAMPLE 12

6-[2-(4-aminobutyl)-1H-benzimidazol-5-yl]-4,5-dihydro-5-methyl-3(2H)-pyridazinone

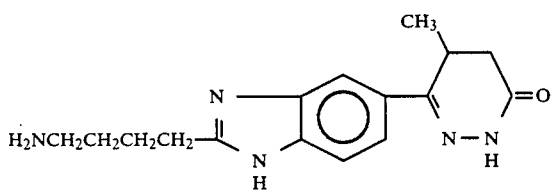

0.54 g (1 26 mmol) of 6-[2-(4-phthalimidobutyl)-1H-benzimidazol -5 yl]-4,5-dihydro-5-methyl-3(2H)-pyridazinone and 0 3 ml (6.3 mmol) of hydrazine hydrate are boiled in 20 ml of ethanol for 2 hours. After cooling to room temperature, the solution is filtered, the filtrate is concentrated by evaporation under vacuum and the residue is taken up with 10 ml of 2N hydrochloric acid. The resulting solution is again filtered and is then adjusted to pH 11 with 3N sodium hydroxide solution and concentrated by evaporation to half its original volume. On cooling in an ice bath, a colorless solid crystallizes, which is recrystallized from ethanol. 0.26 g (69%) of crystals are obtained which melt at 185° to 187° C. and resolidify but thereafter do not melt until heated to 280° C.

$C_{16}H_{21}N_5O$ (299.37).

| $^1$H-NMR data (CD$_3$OD, TMS as internal standard) | δ = 1.2 (d) 3H<br>1.5–2.1 (m) 4H<br>2.3–3.2 (m) 6H<br>3.3–3.7 (m) 1H<br>4.9 (broad) 4H replaceable by D$_2$O<br>7.5–8.2 (m) 3H ppm |
|---|---|

EXAMPLE 13

6-[2-(3-aminopropyl)-1H-benzimidazol-5yl]-4,5-dihydro-3(2H)-pyridazinone

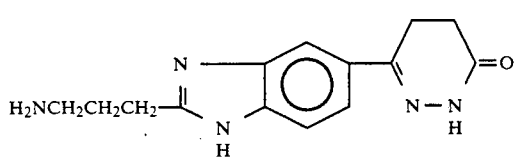

Prepared by a method analogous to that of Example 1d) from 3.3 g (8.2 mmol) of 6-[2-(3-phthalimidopropyl)-1H-benzimidazol-5-yl]-4,5-dihydro-3(2H)-pyridazinone and 2.0 ml (41.1 mmol) of hydrazine hydrate. 0.77 g (35%) of a colorless solid melting at 247° to 249° C. (decomp.) are obtained after chromatographic purification on silica gel with methanol/conc. ammonia (95:5) as solvent, concentration of the main fraction by evaporation under vacuum and crystallization of the residue from ethanol.

$C_{14}H_{17}N_5O$ (271.32).

| $^1$H-NMR data (DMSO-d$_6$, TMS as internal standard) | δ = 1.7–2.1 (quin) 3H<br>2.4–3.2 (m) 8H<br>4.3 (broad) 4H replaceable by D$_2$O<br>7.5–8.1 (m) 3H ppm |
|---|---|

EXAMPLE 14

$N^1$-[3-(imidazol-4-yl)propyl]-$N^2$-[4-[5-(4-methyl-6-oxo-1,4,5,6-tetrahydropyridazin-3-yl)-1H-benzimidazol-2yl]butyl]-guanidine

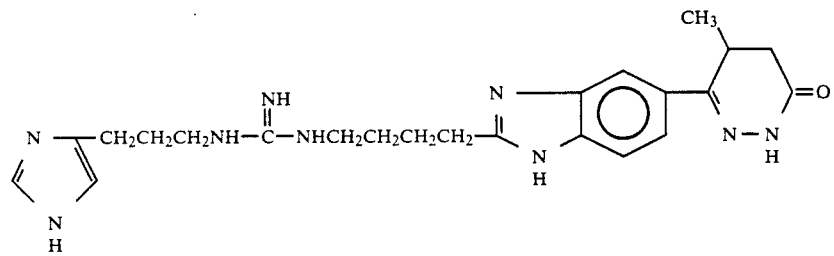

0.48 g (53%) of a colorless, amorphous solid are obtained by a method analogous to that of Example 6 from 1.00 g (2.0 mmol) of N-[4-[5-(4-methyl-6-oxo-1,4,5,6-tetrahydropyridazin -3yl)-1H-benzimidazol-2-yl]butyl]-S-methyl-isothiuronium iodide and 0.25 g (2.0 mmol) of 3-(imidazol-4-yl)propylamine.

$C_{23}H_{31}N_9O$ (449.56).

| $^1$H-NMR data (CD$_3$OD, TMS as internal standard) | δ = 1.2 (d) 3H<br>1.6–3.7(m) 17H<br>5.0 (broad) 6H replaceable by D$_2$O<br>6.95 (s) 1H<br>7.4–8.2 (m) 4H ppm |
|---|---|

EXAMPLE 15

6-[2-[3-(ethoxycarbonylamino)propyl]-1H-benzimidazol-5-yl]-4,5-dihydro-5-methyl-3(2H)-pyridazinone

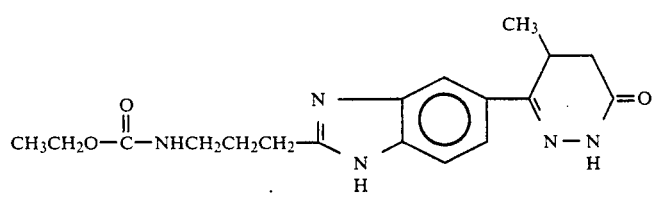

0.45 ml (4 7 mmol) of ethylchloroformate are added dropwise over a period of 10 minutes to a solution of 1 00 g (3.5 mmol) of 6-[2-(3-aminopropyl)-1H-benzimidazol-5-yl]-4,5-dihydro -5-methyl-3(2H)-pyridazinone and 1 25 g (9.0 mmol) of potassium carbonate in 10 ml of acetone and 10 ml of water with cooling in an ice bath. After 3 hours' stirring at room temperature, the reaction mixture is filtered and the filtrate is diluted with 20 ml of water and extracted three times with 20 ml portions of dichloromethane. The combined organic phases are dried and concentrated by evaporation under vacuum and the residue is chromatographed on silica gel with dichloromethane/methanol (9:1) as solvent. The polar main fraction (Rf 0 46) yields 0.65 g (52%) of the title compound in the form of a yellowish, amorphous solid after concentration by evaporation under vacuum.

$C_{18}H_{23}N_5O_3$ (357.41).

| $^1$H-NMR data (CD$_3$OD, TMS as internal standard) | $\delta$ = | 1.1–1.3 (d + t) 6H<br>1.8–2.2 (quin) 2H<br>2.3–3.1 (m) 4H<br>3.25 (t) 2H<br>3.3–3.7 (m) 1H<br>4.1 (q) 2H<br>4.9 (broad) 3H replaceable by D$_2$O<br>7.5–8.1 (m) 3H ppm |
|---|---|---|

We claim:

1. Benzimidazoles corresponding to the formula (I)

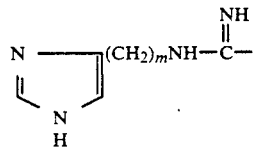

-continued

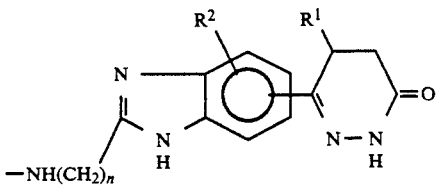

wherein the pyridazinone ring is attached in the 5- or 6-position of the benzimidazole ring and $R^1$ stands for a hydrogen atom or a straight chained or branched $C_1$ to $C_4$ alkyl group, $R^2$ stands for a hydrogen atom, a straight chained or branched $C_1$ to $C_4$ alkyl group, a $C_1$ to $C_4$ alkoxy group, a hydroxy group, a halogen atom, an amino group or a nitro group, m has the value 2 or 3 and n stands for an integer with a value from 1 to 6, and the pharmaceutically acceptable salts thereof.

2. A pharmaceutical preparation comprising a benzimidazole as claimed in claim 1, together with at least one inert, pharmaceutically acceptable carrier or diluent.

3. A benzimidazole according to claim 1, wherein said benzimidazole is $N^1$-[3-(imidazol-4-yl)propyl]-$N^2$-[3-[5-(4-methyl -6-oxo-1,4,5,6-tetrahydropyridazin-3yl)-1H-benzimidazol-2-yl] propyl]-guanidine or pharmaceutically acceptable salts thereof.

4. A benzimidazole according to claim 1, wherein said benzimidazole is 6-[2-(2-aminoethyl)-1H-benzimidazol-5-yl]-4,5-dihydro -5-methyl-3(2H)-pyridazinone or pharmaceutically acceptable salts thereof.

5. A benzimidazole according to claim 1, wherein said benzimidazole is $N^1$-[3-(imidazol-4-yl)propyl]-$N^2$-[2-[5-(4-methyl -6-oxo-1,4,5,6-tetrahydropyridazin-3-yl)-1H-benzimidazol -2-yl]ethyl]-guanidine or pharmaceutically acceptable salts thereof.

6. A benzimidazole according to claim 1, wherein said benzimidazole is $N^1$-[3-(imidazol-4-yl)propyl]-$N^2$-[4-[5-(4-methyl -6-oxo-1,4,5,6-tetrahydropyridazin-3-yl)-1H-benzimidazol -2yl]butyl]-guanidine or pharmaceutically acceptable salts thereof.

* * * * *